United States Patent [19]
Keith

[11] Patent Number: 5,144,957
[45] Date of Patent: Sep. 8, 1992

[54] CUTANEOUS THERAPEUTIC DEVICES
[75] Inventor: Alec D. Keith, Boalsburg, Pa.
[73] Assignee: Zetachron, State College, Pa.
[21] Appl. No.: 682,394
[22] Filed: Apr. 3, 1991

Related U.S. Application Data

[63] Continuation of Ser. No. 469,246, Jan. 24, 1990, abandoned.

[51] Int. Cl.$^5$ .............................................. A61B 15/00
[52] U.S. Cl. ................................... 128/743; 604/304; 206/823
[58] Field of Search ............... 604/289, 290, 304, 307; 128/743; 8/405–408; 132/320, 212; 206/823

[56] References Cited

U.S. PATENT DOCUMENTS

| | | | |
|---|---|---|---|
| 3,212,495 | 10/1965 | Osbourn et al. ................. | 128/743 |
| 4,470,826 | 9/1984 | Bugaut et al. ................... | 8/408 |
| 4,588,400 | 5/1986 | Ring et al. ...................... | 604/304 |
| 4,777,969 | 10/1988 | Holloway ........................ | 206/823 |
| 4,887,611 | 12/1989 | Rüdiger et al. ................. | 604/304 |

OTHER PUBLICATIONS

Abstract of GB2208928, Great Britain (1989).
Abstract of EP0335231 EPO (1989).
Abstract of WO 8809184 (1988).
Abstract of DD 0257585 (1988).
Abstract of JP 62281827, Japan (1987).
Abstract of EP 0252044, EPO (1988).
Abstract of JP 62081315, Japan (1987).
Abstract of WO 8601994, (1980); U.S. Pat. No. 4,836,217 (1989).
Abstract of EP 0165219, EPO (1985).
Fischer et al., *J. Am. Aced. Derm. 20(3): 447–453 (1989).*
Fischer et al., *Immunology and Allergy Clinics of North America,* 9:(3), pp. 417–433 (1989).

*Primary Examiner*—Peter A. Aschenbrenner
*Attorney, Agent, or Firm*—Wegner, Cantor, Mueller & Player

[57] ABSTRACT

An allergic response indicator is provided which comprises a cutaneous three dimensional polymeric sheet capable of self-adherence to the epidermis of a subject and containing an indicator compound distributed throughout said cutaneous three dimensional polymeric sheet which, when applied to said epidermis, is released thereto over the period of application, whereby upon release of said indicator compound an allergic reaction is manifested by visual signs of skin irritation at the site of application upon the removal of said allergic response indicator.

5 Claims, 1 Drawing Sheet

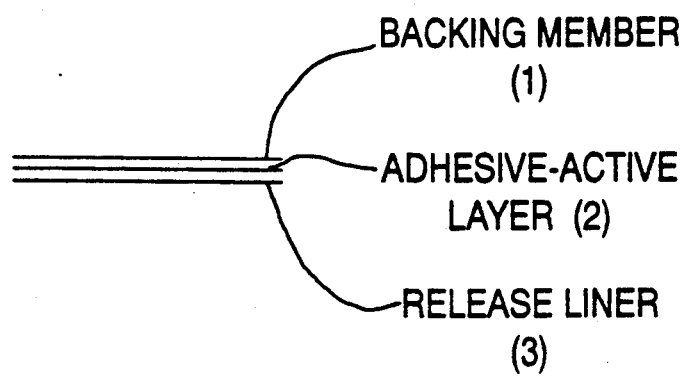
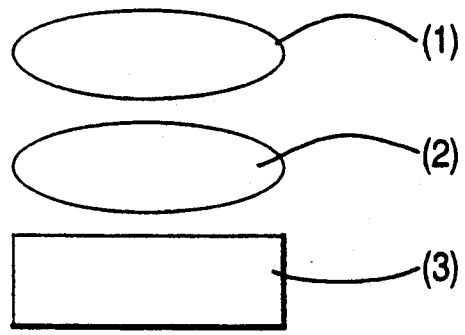
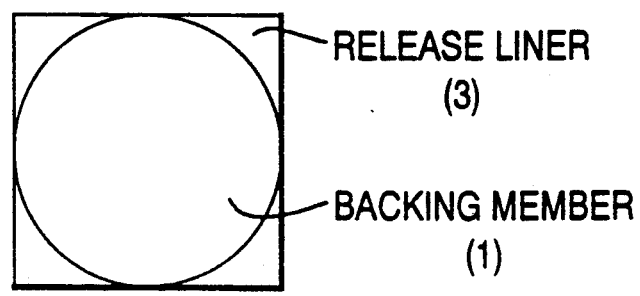

CUTANEOUS THERAPEUTIC DEVICES

This application is a continuation of U.S. application Ser. No. 07/469,246 filed Jan. 24, 1990, now abandoned.

It is known to test for allegeric reactions of chemicals, particularly hair dyes, by swabbing the chemical onto a skin area, and then awaiting a visual sign of an allergic reaction. This is both messy with staining of clothing and, for a hair color manufacturer, unnecessarily expensive due to returned merchandise that must be refunded. It is also known to test in a doctor's office by smearing petroleum jelly containing an irritant onto the skin, and then looking for a reaction. Syringes have been used to apply such a mixture.

In accordance with the present invention there is provided an allergic response indicator which comprises a cutaneous three dimensional polymeric sheet capable of self-adherence to the epidermis of a subject which typically has a very small area, sufficiently large to permit visual inspection for an allergic reaction caused by the chemical which transfers to the skin from the allergic response indicator, and preferably no larger to avoid any unnecessary contact of chemical with the skin. In a preferred embodiment, a circular patch of about 1 cm$^2$ is provided. The allergic response indicator contains an indicator compound distributed throughout said cutaneous three dimensional polymeric sheet which, when applied to said epidermis, is released thereto over the period of application, whereby upon release of said indicator compound an allergic reaction is manifested by visual signs of skin irritation at the site of application upon the removal of said allergic response indicator.

In another embodiment, an allergic response indicator is provided wherein said indicator compound is a hair color to be tested by a potential user prior to application of said hair color to the hair.

The indicator compound may be p-phenylenediamine, which is both itself a hair color as well as being a good indicator of the likelihood that a particular subject will be sensitive to related hair coloring agents.

In accordance with a second aspect of the invention, there is provided a method of testing for an allergic response to a hair color which comprises application of the allergic response indicator of the invention to the skin of a subject, and observation of the skin to visually determine the presence of an allergic reaction.

In a still further embodiment, a kit is provided that comprises the hair color, itself, packaged with an allergic response indicator of the invention.

FIG. 1, shows a stylized side view of the three layers of the invention.

FIG. 2, shows a perspective stylized view of the invention wherein the layers are separated.

FIG. 3, shows a stylized top view of the invention.

EXAMPLE I

In a darkened or red light environment to mitigate against oxidation of chemicals to be tested and which are incorporated into the allergic response indicator of the invention, preferably p-phenylenediamine in an amount of 16.6 mg (1% in the solid matrix) is mixed thoroughly at 20° C. with 50 ml organic non-polar acrylic adhesive and a molecular weight of approximately 4,000 (having 33 percent solids and the remainder ethyl acetate) having at least about 95 percent of the acid groups blocked by esterification with a methyl or ethyl alcohol, such as Gleva Resin Solution 737 (Monsanto). 1.6 mg adipic acid dissolved in 1 ml ethyl acetate is added to this resultant mixture. Intimate mixture of the ingredients takes place, followed by spreading onto a release liner (3) to a thickness of 12 mil. Drying through solvent evaporation at a temperature of from 25° C. to 40° C. is permitted to occur so that a solid product is obtain having a thickness of 4 mil.

An opaque backing member (1) is then laid onto the adhesive (2) through a compression roller. The resultant sheet is then cut into circular patches of the desired area.

Each patch is unit packaged in an opaque aluminum pouch that has been packaged under a nitrogen environment.

Into a box having a typical unit of hair color for sale through retail distribution means there is included a thus individually packaged allergic response indicator.

The subject typically applies the allergic response indicator by peeling off the release liner (3), and the allergic response indicator onto his or her upper arm before retiring for the evening, and upon awakening will peel off the patch to reveal either normal skin, indicating that there is no allergic reaction, or a colored skin area, indicating irritation and contra-indication of the hair color product.

EXAMPLE II

In Example I, instead of the 16.6 mg (1% in the solid matrix) p-phenylenediamine of Example 1, the amount of p-phenylenediamine is reduced so that the final solid will have 0.3% p-phenylenediamine. Additionally, the amount of adipic acid used is 0.5 mg, and otherwise the conditions of Example I are used.

EXAMPLE III

In Example I, instead of the 16.6 mg (1% in the solid matrix) p-phenylenediamine of Example 1, the amount of p-phenylenediamine is reduced so that the final solid will have 0.1% p-phenylenediamine. Additionally, the amount of adipic acid used is 0.16 mg, and otherwise the conditions of Example I are used.

EXAMPLE IV

One part ethyl cellulose and two parts ethyl ester of 6,000 molecular weight acrylic acid are blended together. 50 ml of this mixture (having 33 percent solids and the remainder ethyl acetate) is substituted for the organic non-polar acrylic adhesive of Example I to yield a second embodiment of the invention.

What is claimed is:

1. An allergic response indicator which comprises a cutaneous three dimensional polymeric sheet capable of self-adherence to the epidermis of a subject and containing an indicator compound distributed throughout said cutaneous three dimensional polymeric sheet which, when applied to said epidermis, is released thereto over the period of application, whereby upon release of said indicator compound an allergic reaction is manifested by visual signs of skin irritation at the site of application upon the removal of said allergic response indicator, said polymeric sheet being composed of a material that provides said self-adherence.

2. An allergic response indicator of claim 1 wherein said indicator compound is a hair coloring agent to be tested by a potential user prior to application of said hair coloring agent to the hair.

3. An allergic response indicator of claim 2 wherein said indicator compound is p-pheylenediamine.

4. A method of testing for an allergic response to a hair color which comprises application of an allergic response indicator comprising a cutaneous contact adhesive three dimensional polymeric sheet capable of self adherence to the epidermis of a subject and containing an indicator compound distributed throughout said cutaneous three dimensional polymeric sheet, to the skin of a subject, and observation of the skin to visually determine the presence of an allergic reaction.

5. A kit for the distribution and allergic testing of a hair coloring agent which comprises a container of hair dye and an allergic response indicator comprising a cutaneous three dimensional contact adhesive polymeric sheet capable of self adherence to the epidermis of a subject, said polymeric sheet being composed of a material that provides said self-adherence and containing an indicator compound distributed throughout said cutaneous three dimensional polymeric sheet.

* * * * *